United States Patent [19]

Neuwirth

[11] 4,389,192
[45] Jun. 21, 1983

[54] DENTAL REDUCING TOOL

[76] Inventor: Siegmund A. Neuwirth, 30 St. George's Rd., Golders Green, London NW11 OLR, England

[21] Appl. No.: 257,916

[22] Filed: Apr. 27, 1981

Related U.S. Application Data

[63] Continuation-in-part of Ser. No. 67,794, Aug. 20, 1979, Pat. No. 4,264,307.

[51] Int. Cl.³ ............................................. A61C 3/02
[52] U.S. Cl. .................................................. 433/166
[58] Field of Search ............ 433/166, 165; 51/206 R; 408/144; 76/108 R, 108 T; D19/12

[56] References Cited

U.S. PATENT DOCUMENTS 3,510,990  5/1970  Steindler ........................ 51/205 R
4,178,689  12/1979  Nash .................................. 433/166

FOREIGN PATENT DOCUMENTS 902944  9/1945  France ............................... 433/166

Primary Examiner—Robert Peshock
Attorney, Agent, or Firm—Bernard Malina

[57] ABSTRACT

A dental tool for reducing tooth structure includes a shaft adaptable to be carried by rotating means at one end thereof and a shank extending axially from the other end of the shaft. In one group of embodiments thereof, the shank has a plurality of non-intersecting grooves forming a plurality of reducing elements spaced along the length of the shank. Each of the grooves in axial cross-section of the shank has a rounded bottom wall while the reducing elements may have one of various configurations. In another group of embodiments thereof, the shank is helically grooved to define a reducing element with the crest thereof centered on the shank axis.

5 Claims, 14 Drawing Figures

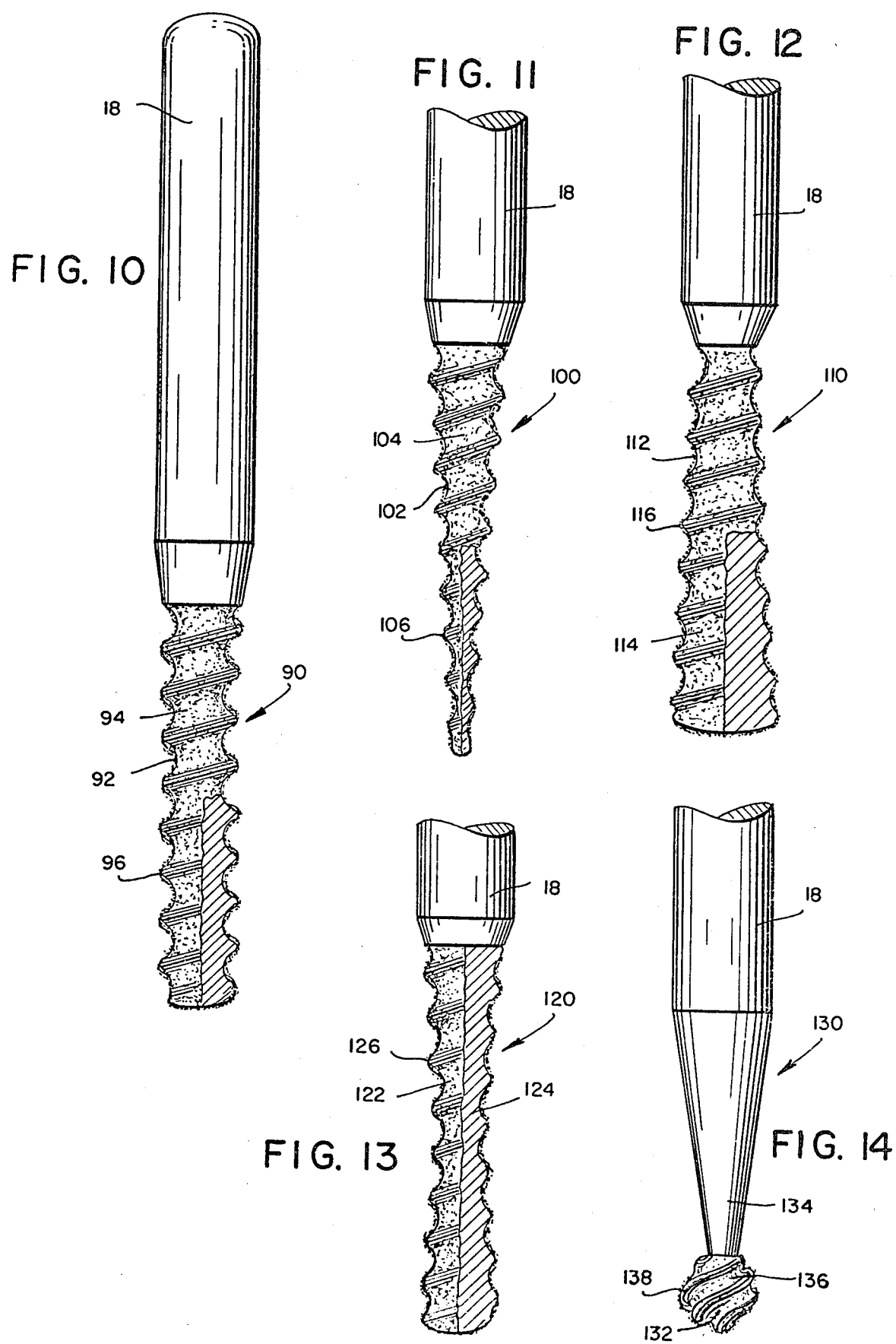

DENTAL REDUCING TOOL

BACKGROUND OF THE INVENTION

This application is a continuation-in-part of my co-pending application Ser. No. 67,794 filed Aug. 20, 1979, now U.S. Pat. No. 4,264,307.

The present invention relates to dental instruments and more particularly to dental instruments for use in tooth structure reduction operations.

In the course of dental repairing operations such as the reduction of tooth enamel for the fitting of a jacket crown or the provision of a suitable opening in the tooth for an inlay or filling, the dentist commonly employs a handheld power driven grinding tool. Such grinding tools usually comprise a rotary driven shaft having a shank portion provided with an abrasive coating on its peripheral face which serves as the grinding portion. Ordinarily, due to the frictional engagement of the instrument grinding portion therewith, substantial heat is produced at the tooth surface which can cause substantial patient discomfort. Such grinding action also requires the application of steady pressure of the grinding portion against the tooth enamel dentin or filling necessitating prolonged and constant exertion by the dentist, to the detriment of both the patient and the dentist's work efficiency.

The above-mentioned disadvantages have been found to be virtually unavoidable in the use of currently available dental grinding tools because the design of their grinding portion does not permit the rapid reduction of axial walls occlusal surfaces in crown preparation or the rapid opening or extending of new cavities, or in the removal of old composite or amalgum fillings.

It has also been found that in the use of conventional tooth grinding tools, tooth debris formed during axial wall reduction and cavity preparation operations tend to accumulate and clog the sharp corners and crevices in the working portion of the tool thereby impairing the cutting quality of the tool and substantially reducing tool life.

It is, therefore, an object of the present invention to provide a dental reducing tool which enables rapid reduction and penetration of the tooth structure with minimal generation of heat on the tooth.

It is a further object of the present invention to provide a dental reducing tool of the character described which minimizes accumulation of tooth debris on the tool and facilitates efficient removal of such debris which may have formed thereon during the various tooth structure reducing processes.

SUMMARY OF THE INVENTION

In accordance with the principles of the present invention, there is provided a tool for reducing tooth structure comprising a shaft adaptable to be carried by rotating means at one end thereof and a shank extending axially from the other end of said shaft. In one group of embodiments thereof a plurality of parallel coaxial grooves formed in the shank define a plurality of reducing elements spaced along the length of said shank, each of said grooves having a rounded bottom wall. In another group of embodiments thereof, the surface of the shank is helically grooved to define a reducing element with the crest thereof lying on a helix centered on the axis of the shank. The working surfaces of said reducing elements may be coated with a suitable abrasive material to provide an efficient cutting surface.

Further objects, features and advantages of the invention will become apparent from a consideration of the following description, the appended claims and the accompanying drawings in which:

BRIEF DESCRIPTION OF THE DRAWINGS

FIG. 10 is an enlarged fragmentary section view of a reducing tool in accordance with the present invention in a fifth embodiment thereof wherein the reducing element is helical, and the configuration thereof is cylindrical;

FIG. 11 is an enlarged fragmentary section view of a reducing tool in accordance with the present invention in a sixth embodiment thereof wherein the reducing element is helical and the configuration thereof is inwardly tapered;

FIG. 12 is an enlarged fragmentary section view of a reducing tool in accordance with the present invention in a seventh embodiment thereof wherein the reducing element is helical and the configuration thereof is frusto-conical;

FIG. 13 is an enlarged fragmentary section view of a reducing tool in accordance with the present invention in an eighth embodiment thereof wherein the reducing element is helical and the configuration thereof is partially inwardly tapered and partially outwardly tapered; and FIG. 14 is an enlarged fragmentary section view of a reducing tool in accordance with the present invention in a ninth embodiment thereof wherein the reducing element is helical and the configuration thereof is spheroidal.

DETAILED DESCRIPTION OF THE INVENTION

Figure 1:
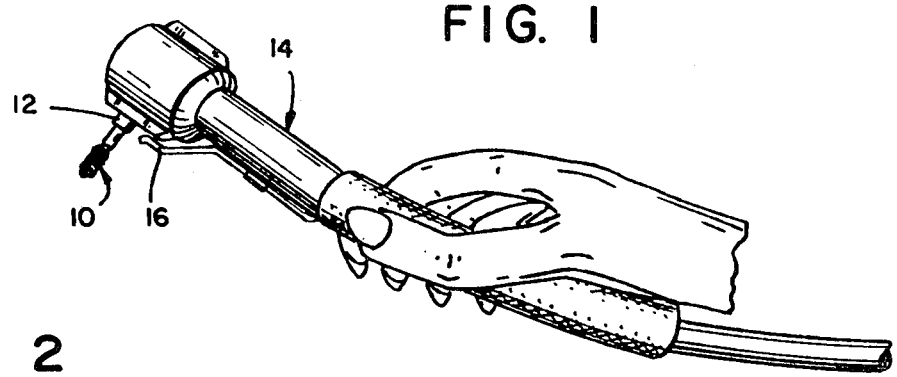
FIG. 1 is a perspective view of a conventional dental handpiece mounted thereto a dental reducing tool constructed in accordance with the present invention.

Referring to the drawings and in particular to FIG. 1 thereof, the present dental reducing tool designated generally by the numeral 10 is adapted to be mounted in the chuck 12 of a dental handpiece 14 of conventional construction. Dental handpiece 14 is operative to rotate the chuck 12 at high speed and is ordinarily provided with a nozzle 16 for directing streams of fluid, usually comprising water or water and air, upon the reducing tool 10 and the tooth area for cooling the latter and washing away grinding debris which may fall on the cutting surface of the reducing tool 10.

Figure 2:
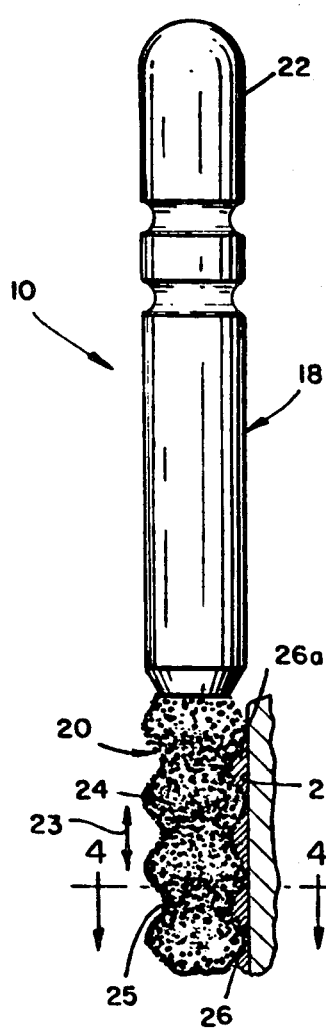
FIG. 2 is an enlarged elevational view of a dental reducing tool constructed in accordance with the present invention in one embodiment thereof.
Figure 4:
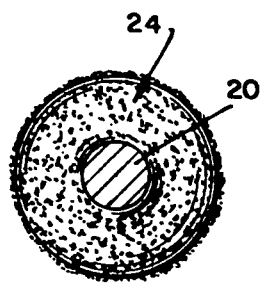
FIG. 4 is a section view taken along the line 4—4 in FIG. 3.
Figure 3:
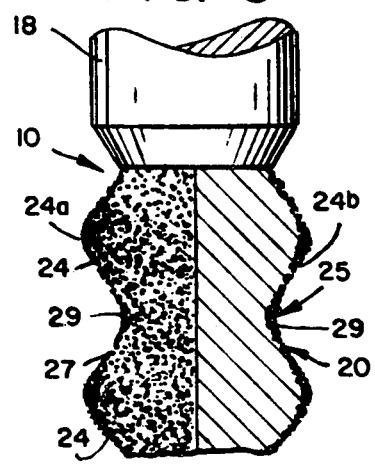
FIG. 3 is a further enlarged fragmentary section view showing in greater detail the structure of the reducing elements of the tool of FIG. 2.

In one embodiment thereof, the reducing tool 10 of the present invention best shown in FIGS. 2 and 3, comprises a shaft 18 having a generally cylindrical end 22 adapted for detachable frictional engagement with the chuck 12 of the handpiece 14 and a grooved shank portion 20 at its opposite end, forming a plurality of coaxial circular grinding or reducing elements 24 spaced along the length of shank portion 20. In FIG. 2, shank portion 20 is illustrated as having six grooves forming seven reducing elements 24; it is to be understood, however, that more or less reducing elements 24 may be provided in accordance with particular requirements.

Shaft 18 may be formed of steel or other appropriate material. In order to provide a suitable abrasive grinding surface, the surfaces of the grinding elements 24 and the grooves 25 separating the elements 24 may be coated with a uniform layer 27 of abrasive material such as diamond particles embedded in a metal base as shown in FIG. 2. The composition and method of application of such abrasive layer to the cutting surfaces of shank 20 is well known and hence need not be described herein.

Figure 5:
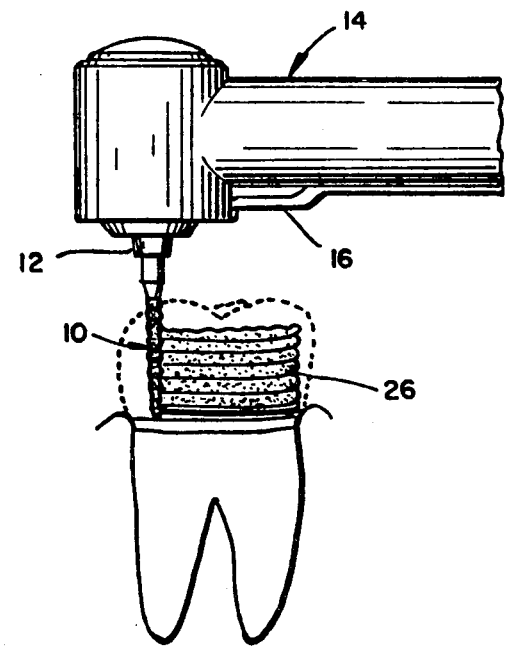
FIG. 5 is an elevational view illustrating the use of the tool of FIG. 3 in one step of crown preparation.
Figure 6:
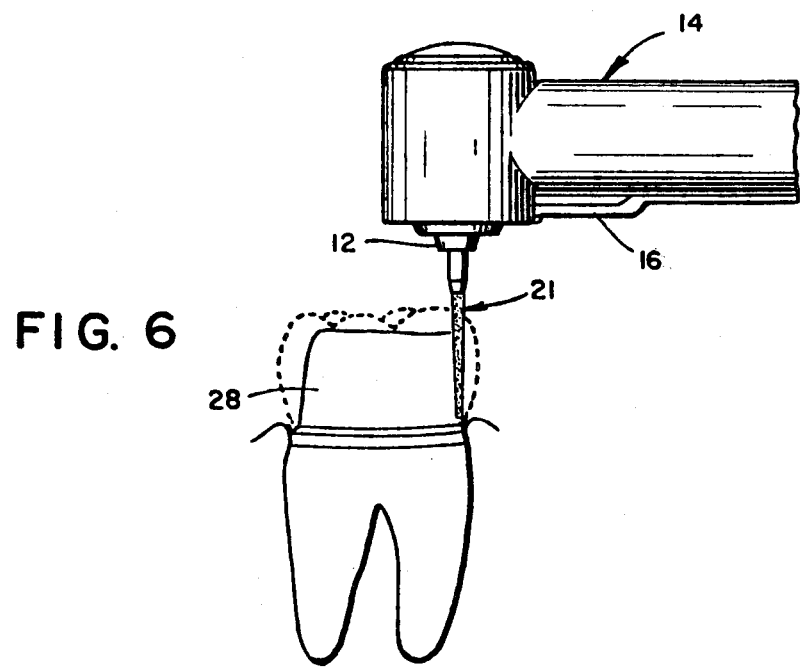
FIG. 6 is an elevational view illustrating the use of a conventional tool to smooth the axial walls of the tooth in a step subsequent to that shown in FIG. 5.

In operation, shaft 18 is brought up to suitable rotational speed by manipulation of handpiece 14 and shank 20 is then brought to bear against the tooth structure 26 (FIG. 2) in a direction perpendicular to the longitudinal axis of shank 20. The foregoing action is continued until the reducing elements 24 penetrate to a desired depth into the tooth substrate thus forming a laterally grooved surface having tooth substrate peaks 26a. In the case of tooth reduction for crown preparation, as shown in FIG. 5, the working surface of rotating tool 10 may be applied continuously across the tooth surface to be reduced. In one alternative operation reducing tool 10 may then be moved to-and-fro in a plane parallel to the longitudinal axis of the shank 20 in the direction of arrow 23 so that the side wall 24b of elements 24 clear away the remaining ridges 26a in a lateral grinding action thereby providing a clean tooth surface 28. In another alternative operation reducing tool 10 may be replaced by a straight taper reducing tool 21 to clear away the ridges 26a as shown in FIG. 6.

During the course of the aforementioned cutting operation, the stream of fluid applied by nozzel 16 causes the tooth debris to be easily flushed away from the tooth surface as well as from the surface of the reducing elements 24.

The reducing tool 10 of FIGS. 2 and 3 provides optimum ease of penetration of the tooth substrate 26 with minimal generation of heat on the tooth structure and facilitates flushing of tooth debris from the work surfaces. In order to achieve such performance, the abrasive coated reducing elements 24 have curved ridges 24a and side walls 24b which taper away from each other in the direction of the shaft rotation axis and the grooves 25 have curved bottom walls 29. The rounded and tapered crests 24a of elements 24 provide easy and gradually-widening penetration of tooth substrate 26 thereby minimizing frictional contact resistance with the tooth surface and attendant heat build up. The rounded bottom walls 29 and tapered sidewalls 24b of grooves 25 tend to prevent tooth debris from embedding therein and clogging the grinding tool and, furthermore, facilitates the easy and complete removal of any such debris which may have accumulated during the grinding operation, by the flushing action of the cleansing and cooling fluid stream from nozzle 16.

Although in axial cross-section thereof, elements 24 and grooves 25 both have tapering side walls and curved crests and bottom walls respectively, it should be understood that the respective degrees of taper and crest and bottom wall widths may differ. Thus, for example, the width of element 24 may be narrower than the corresponding grooves 25 to provide quicker penetration of very hard tooth structure with less pressure while providing less opportunity for the buildup of potentially clogging debris in the grooves 25.

Figure 7:
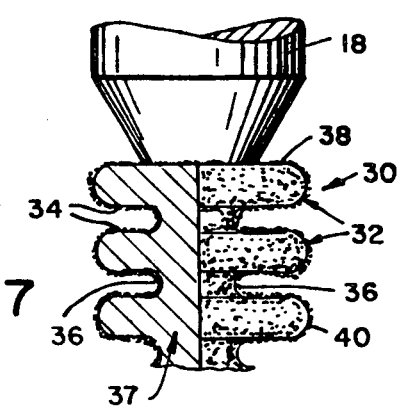
FIG. 7 is an enlarged fragmentary section view showing in detail the structure of the reducing elements of a reducing tool constructed in accordance with the present invention in a second embodiment thereof.

Another embodiment of the present invention is illustrated in FIG. 7 which may be considered as a variant of the reducing tool 10 of FIGS. 2 and 3. Referring to FIG. 7, the reducing tool 30 comprises reducing elements 32 in the form of flat discs having substantially parallel side walls 34 and circularly rounded groove bottom walls 36 formed in shank 37. As in the device of FIG. 2, elements 32 including the side walls 34 and groove bottom walls 36 are provided with a substantially uniform thickness coating 38 of abrasive material comprising diamond particles embedded in a metal base. The rims 40 of reducing elements 32 are relatively blunter than the rims 24a of the reducing elements 24, a feature which is useful in some dental reducing applications, particularly when the dentist is dealing with a normal or standard tooth structure hardness. Furthermore, the parallel relationship of side walls 34 produces substantially parallel grooves of uniform width having rounded inner ends of similar width in the tooth structure, which may be particularly desirable in some situations. The above-described configuration of reducing elements 32 provides greater initial reduction of tooth structure while maintaining sufficient penetration capability for tooth structure of normal hardness.

Figure 8:
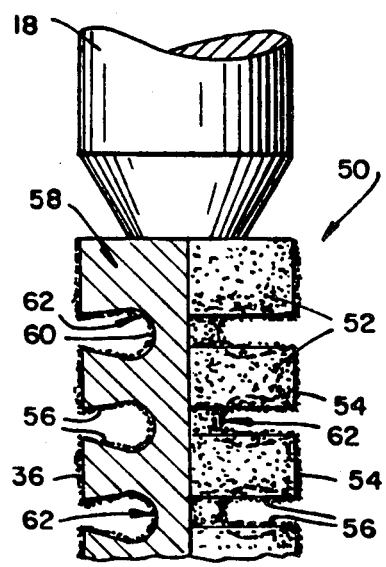
FIG. 8 is an enlarged fragmentary section view showing in detail the structure of the reducing elements of a reducing tool constructed in accordance with the present invention in a third embodiment thereof.

In yet another embodiment of the present invention illustrated in FIG. 8, the reducing tool 50 is formed with circular reducing elements 52, each of which in axial cross-section has peripheral edges or rims 54 which are substantially flat, and side walls 56 which taper inwardly toward the axis of rotation of shank 58 for a major portion of their length and then continue into the circularly rounded groove inner walls 60 of adjacent grooves 62. The reducing tool 50 of FIG. 8 is particularly effective in use on soft tooth structure to provide greater reducing action while the rounded groove inner walls 60, as before, prevent an accumulation of tooth debris in the tool and facilitate removal of any such debris by the action of the cleaning and cooling fluid stream from nozzle 16.

Figure 9:
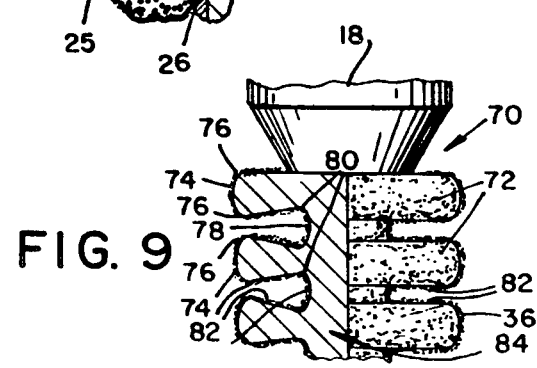
FIG. 9 is an enlarged fragmentary section view showing in detail the structure of the reducing elements of a reducing tool constructed in accordance with the present invention in a fourth embodiment thereof.

In a further embodiment of the present invention shown in FIG. 9, the reducing tool 70 comprises reducing elements 72 each of which in cross-section has substantially flat rim 74, the edges 76 of which are rounded, and a similarly shaped groove inner wall; i.e. having a slightly rounded surface 78 and gently rounded end portions 80. As in tool 50 shown in FIG. 8, the side walls 82 of elements 72, taper inwardly toward the axis of rotation of shank 84. The reducing tool of FIG. 9 is suitable for use on quite soft tooth structure and thin layer of enamel and dentin for maximum reduction capability.

As in the embodiments of FIGS. 3 and 7, the grinding tools 50 and 70 of FIGS. 8 and 9 may be provided with a coating 36 of abrasive material comprising diamond particles embedded in a metal base.

It is understood that the present invention in the embodiments of FIGS. 2, 3, 7, 8 and 9 is not limited to reducing tools having reducing elements of uniform diameter, i.e. overall cylindrical shape in radial cross-section of the shank. Thus, the invention may be embodied in reducing tools of the character described above having a radial cross-section of the shank, various shapes such as spheroidal or ellipsoidal shapes.

In still further embodiments of the invention shown in FIGS. 10–14, the reducing tools 90, 100, 110, 120 and 130 each have single helical grooves, 92, 102, 112, 122 and 132 respectively formed in the shanks thereof. In FIG. 10, the shank 94 is of overall cylindrical configuration whereby the periphery of the reducing element 96 defines a cylindrical configuration.

In the embodiment of FIG. 11 the shank 104 tapers inwardly in the direction away from the shaft 18 while in the embodiment of FIG. 12, the shank 114 tapers outwardly in the direction away from the shaft 18.

FIG. 13 shows another embodiment in which the shank 124 initially tapers inwardly for a predetermined length and thereafter tapers outwardly in the direction away from the shaft.

In yet another embodiment shown in FIG. 14, the initial shank portion 134 tapers inwardly and is provided with a spherical working portion 136 at the end thereof remote from the shaft. Helical groove 132 is formed in the working portion 136 while the initial shank portion 134 is ungrooved.

In each of the above described tools 90, 100, 110, 120 and 130, the reducing elements 96, 106, 116, 126 and 138 are coated with suitable abrasive material.

In some applications, the tools of FIGS. 10–14 having helical reducing elements 96, 106, 116, 126 and 138 respectively, are particularly effective in removing tooth debris away from the working area of the tooth and thereby avoiding clogging problems. The spiral grooves 92, 102, 112, 122 and 132 respectively channel the stream of fluid, such as water, therethrough, which carries with it accumulated debris in a spiral path down the length of the shank. This spiral travel path of the fluid stream also improves cooling efficiency because it causes the stream to contact virtually the entire length of the tooth working area.

Furthermore, the spiral configuration of the reducing elements 96, 106, 116, 126 and 138 enables tooth reduction to be accomplished in one operation by applying the length of the tools 90, 100, 110, 120 and 130 respectively against the tooth surface as shown in FIG. 5. Unlike the embodiments of FIGS. 2, 3, 7, 8 and 9 no ridges are formed as the result of said operation thus obviating the necessity of a second to-and-fro grinding operation in the direction of arrow 23 in FIG. 2.

While preferred embodiments of the invention have been shown and described herein, it is to be understood that such embodiments are merely illustrative of the application of the principles of the invention. Numerous modifications may be made therein and other arrangments may be devised without departing from the spirit and scope of the invention.

What is claimed is:

1. A tool for removing tooth structure comprising:
   a shaft adaptable to be carried by rotating means at one end thereof, a shank extending axially from the other end of said shaft, the surface of said shank being helically grooved to define a reducing element with the crest thereof lying on a helix centered on the axis of said shank, and the working surface of said reducing element being coated with a suitable abrasive material, the periphery of said reducing element tapering outwardy in the direction away from said shaft.

2. A tool for removing tooth structure comprising:
   a shaft adaptable to be carried by rotating means at one end thereof, a shank extending axially from the other end of said shaft, the surface of said shank being helically grooved to define a reducing element with the crest thereof lying on a helix centered on the axis of said shank, and the working surface of said reducing element being coated with a suitable abrasive material, the periphery of said reducing element tapering inwardly in the direction away from said shaft for a predetermined length of said shank and thereafter tapers outwardly in the direction away from said shaft.

3. A tool as defined in claims 1 or 2 wherein the periphery of said reducing element defines a cylindrical configuration.

4. A tool as defined in claims 1 or 2 wherein the periphery of said reducing element defines a spheroidal configuration.

5. A tool as defined in claims 1 or 2 wherein the helical groove defines a pair of sidewalls respectively forming a substantially continuous surface with the crest of said reducing element.

* * * * *